United States Patent [19]

Bagasra et al.

[11] Patent Number: 5,750,347
[45] Date of Patent: May 12, 1998

[54] IN SITU POLYMERASE CHAIN REACTION

[75] Inventors: Omar Bagasra, Laurel Springs, N.J.;
Roger J. Pomerantz, Chalfont, Pa.

[73] Assignee: Thomas Jefferson University, Philadelphia, Pa.

[21] Appl. No.: 764,538

[22] Filed: Dec. 12, 1996

Related U.S. Application Data

[62] Division of Ser. No. 225,491, Apr. 11, 1994, Pat. No. 5,589,333, which is a continuation of Ser. No. 829,912, Feb. 3, 1992, abandoned.

[51] Int. Cl.$^6$ .............................. C12Q 1/68; C12Q 1/70; C12P 19/34; C07H 21/04
[52] U.S. Cl. ................... 435/6; 435/5; 435/91.2; 435/91.1; 435/7.2; 536/23.1; 536/24.3; 536/24.32; 536/24.33
[58] Field of Search ........................ 364/500; 422/104, 422/102; 211/41; 356/244; 359/391, 398; 435/6, 5, 91.2, 7.1, 7.9; 536/23.1, 24.3, 24.32, 24.33

[56] References Cited

U.S. PATENT DOCUMENTS

| | | | |
|---|---|---|---|
| 5,008,182 | 4/1991 | Sninsky et al. | 435/5 |
| 5,192,503 | 3/1993 | McGrath et al. | 422/57 |
| 5,273,905 | 12/1993 | Muller et al. | 435/301 |
| 5,382,511 | 1/1995 | Stapleton | 435/6 |

FOREIGN PATENT DOCUMENTS

| | | |
|---|---|---|
| 388 171 | 9/1990 | European Pat. Off. . |
| WO 8911547 | 11/1989 | WIPO . |
| WO 9001547 | 2/1990 | WIPO . |
| WO 9002821 | 3/1990 | WIPO . |
| WO 9003443 | 4/1990 | WIPO . |
| WO 9003444 | 4/1990 | WIPO . |
| WO 9102817 | 3/1991 | WIPO . |

OTHER PUBLICATIONS

Clouse et al. Monokine Regulation of Human Immunodeficiency Virus–1 Expression In a Chronically Infected Human T. Cell Clone *J. Immunol.* 1989 142:431.

Folks et al. Cytokine–Induced Expression of HIV–1 in a Chronically Infected Promonocyte Cell Line *Science* 1987 238:800.

Haase et al. Amplification and detection of lentiviral DNA inside cells *Proc. Natl. Sci.* 1990 87:4971.

Harper et al. Detection of lymphocytes expressing human T–lymphotropic virus type III in lymph nodes and peripheral blood from infected individuals by in situ hybridization *Proc. Natl. Acad. Sci.* 1986 83:772.

Schnittman et al. The Reservoir for HIV–1 in Human Peripheral Blood is a T Cell That Maintains Expression of CD4 *Science* 1989 245:305.

Schnittman et al. Increasing Viral Burden in CD4+ T Cells from Patients with HIV Infection Reflects Rapidly Progressive Immunosuppression and Clinical Disease *Ann. Int. Med.* 1990 113:438.

Spector et al. Human Immunodeficiency Virus DNA is Present in a High Percentage of CD4+ Lymphocytes of Seropositive Individuals *J. Infect. Dis.* 1991 164:470.

Sundstrom et al. Establishment and Characterization of a Human Histocytic Lymphoma Cell Line *Int. J. Cancer* 1976 17:565.

Bagasra, O. Amplifications a Forum for PCR Users Polymerase Chain Reaction in situ Mar. 1990 Issue 4 pp. 20–21.

Embretson et al. PCR Amplification of Viral DNA and Viral Host Cell mRNAs in Situ *The Polymerase Chain Reaction* 1994 Birkhauser Boston.

Bagasra et al. Detection of Human Immunodeficiency Virus Type 1 Provirus in Mononuclear Cells by IN Situ Polymerase Chain Reaction *New Eng. J. Med.* 1992 326:1385.

Bagasra et al. anti–Human Immunodeficiency Virus Type 1 Activity of Sulfated Monosaccharides *J. Infect. Dis.* 1991 164:1082.

Nagai et al. Detection of Papillmavirus Nucleic Acids in Genital Precancers with the In Situ Hybridization Technique *Internat'l Jour of Gynec. Path.* 1987 6:366–379.

Godard C. Improved Method for Detection of Cellular Transcripts by in situ Hybridization *Histochemistry* 1983 77:123–131.

Nuovo et al. Importance of Different Variable for Enhancing in situ Detection of PCR–amplified DNA *PCR Methods and Applications* 1993 2:305–312.

Nuovo et al. Detection of Human Papillomavirus DNA in Formalin–fixed Tissues by In Situ Hybridization After Amplification by Polymerase Chain Reaction *Journal of Pathology* 1991 39:847–854.

Nuovo et al. Improved Technique for the In Situ Detection of DNA After Polymerase Chain Reaction Amplification *American Journal of Pathology* 1991 139:1239–1244.

*Primary Examiner*—Stephanie W. Zitomer
*Assistant Examiner*—Dianne Rees
*Attorney, Agent, or Firm*—Woodcock Washburn Kurtz Mackiewicz & Norris LLP

[57] ABSTRACT

The present invention concerns in situ polymerase chain reaction and provides methods and reagents for identifying cells containing at least one selected nucleic acid sequence which may be derived from the human immunodeficiency virus.

16 Claims, 1 Drawing Sheet

IN SITU POLYMERASE CHAIN REACTION

This application is a divisional application of U.S. patent application Ser. No. 08/225,491 filed Apr. 11, 1994 now U.S. Pat. No. 5,589,333 which is a continuation of U.S. patent application 07/829,921, now abandoned, filed Feb. 3, 1992.

BACKGROUND OF THE INVENTION

Advances in nucleic acid research during the past decade have considerably simplified the assays which utilize DNA and RNA probes for research and diagnostic purposes. Among various assays, the recently introduced modification of the gene amplification method called polymerase chain reaction (PCR) qualifies as a technological breakthrough. PCR in an in vitro gene amplification method whereby the DNA from a selected region of a genome can be amplified by more than a million-fold in a few hours, provided that at least a portion of its nucleotide sequences are already known. Segments of the gene sequence that are at both sides of the portion of the gene which one wishes to amplify, are usually synthesized by an automatic DNA synthesizer. These two oligonucleotides, called "primers", are usually 10–30 base pairs (bp) long. The primers hybridize to opposite strands of DNA, and flank the region of interest in the target DNA.

The PCR method has advantages over serological testing. For example, PCR has been used to detect HIV-1 exposure in the seronegative sexual partners of HIV-1-seropositive individuals, in HIV-1-seronegative infants and children, and in health care workers accidently exposed to HIV-1-positive blood or body fluids.

There are several disadvantages in the conventional DNA-PCR method. Due to the sensitivity of the method, a small amount of contamination (usually from DNA fragments aerosolized during a previously performed amplification) may cause a false positive result. Current methods also do not permit determination of which cell types carry a certain gene.

The ability to identify individual cells, either latently or productively infected, under the microscope would be extremely useful in delineating a latent state and emergence from it. This would be useful, not only in understanding the development of infection, but also as a more direct quantitative measure of the effects of antiviral therapy, and as an aid in understanding the mechanism of transmission of HIV-1.

Since the first description of human immunodeficiency virus type I (HIV-1) as the etiologic agent of AIDS, the numbers of cells infected in viva with HIV-1 isolated from individuals at various clinical stages of disease have been evaluated. These studies sought to correlate levels of HIV-1 with disease pathogenesis and to determine the clinical course of HIV-1-seropositive individuals.

The most detrimental clinical consequence of infection with HIV-1 is the severe depletion of CD4-positive lymphocytes. It was assumed that such depletion was the result of selective infection and destruction of CD4-positive lymphocytes by HIV-1. The studies of Harper et al., *Proc. Natl. Acad. Sci. USA*, 83:772–6 (1986), demonstrated that by using in situ hybridization for HIV-1-specific RNA, one can identify only 1:10,000 to 1:100,000 peripheral blood mononuclear cells (PBMC) and lymph node cells positive for HIV-1 in vivo. These studies did not discount the possibility that HIV-1 may be present in a latent proviral form not expressing viral mRNA. The teaching of Harper et al. did not eliminate the possibility that HIV-1 selectively expressed only low levels of multiply-spliced RNA and did not express unspliced genomic HIV-1 RNA. The findings of Harper et al. taken with observations that the rate of isolation of HIV-1 from infected individuals was low, suggested that indirect mechanisms might mediate HIV-1-induced CD4-positive lymphocyte destruction. Several mechanisms have been proposed to account for the severe depletion of CD4-positive lymphocytes including: (1) production of direct cytopathic effect of HIV-1 on CD4-positive cells; (2) generation of HIV-1-specific cytotoxic T-lymphocytes (CTL) or antibody-dependent cellular cytotoxicity (ADCC), which destroy cells expressing surface HIV-1-specific proteins; (3) generation of giant cell syncytia formation, secondary to an interaction of the CD4 receptor and a fusion domain of the HIV-1 envelope glycoproteins; and/or (4) production of antibodies against T lymphocytes, bone marrow stem cells or immature thymocytes.

Recent data suggest a higher level of PBMC containing HIV-1-specific RNA in infected individuals. Studies utilizing limiting dilution assays have shown that infectious HIV-1 can be isolated from an average of 1 in 400 PBMC obtained from patients with AIDS, however, higher viral levels have been detected during acute HIV-1 seroconversion.

Since the introduction of Taq, the thermostable polymerase which brought convenience to the polymerase chain reaction (PCR) method, special attention has been directed to the study of HIV-1 infection using this method. Modifications of the PCR method have been used to quantitatively or semi-quantitatively assess the relative frequencies of HIV-1-infected cells in PBMC, lymph nodes and other cell types. Schnittman et al., *Science*, 245:305–8 (1989); *Ann. Int. Med.*, 113:438–43 (1990), disclose using a combination of cell sorting and quantitative DNA-PCR techniques to observe that at least 1% of CD4-positive lymphocytes in patents with AIDS are infected with HIV-1. For patients who are HIV-1 asymptomatic, the levels of CD-4-positive lymphocytes was shown to be between 1:100 and 1:100,000.

Spector et al., *J. Infect. Dis.*, 164:4703–5 (1991), disclose using a "booster" PCR method and have calculated that at least 10% of CD4-positive lymphocytes carry HIV-1 provirus in AIDS and symptomatic HIV-1-infected patients, whereas a relatively lower proportion of CD4-positive lymphocytes are positive in HIV-1-seropositive individuals.

Studies utilizing a quantitative DNA PCR technique have suggested that there is a correlation between the clinical stage of HIV-1 infection and the level of HIV-1-specific PCR signals.

A current limitation to PCR methodologies utilizing isolated DNA is that one cannot directly associate the amplification results to a specific cell type or easily measure the percentage of cells which carry the target sequence. The HIV-1 virus has been demonstrated to infect CD4-positive lymphocytes, CD8-positive lymphocytes, monocytes, fibroblasts and glial cells in vivo. The CD4-positive lymphocyte is believed to be the primary reservoir for HIV-1 in the bloodstream and cells of the monocyte/macrophage lineage are believed to be the major virus reservoir in solid tissues. Therefore, it is highly desirable to identify all cell types which carry the virus in vivo and determine which cells actively produce HIV-1.

Haase et al., *Proc. Natl. Acad. Sci. USA*, 87:4971–5 (1990), disclose the development of an in situ PCR methodology for Visna virus, a viral pathogen of sheep. Moreover, Haase et al. teach in situ PCR performed on cells infected with Visna virus in suspension. Haase et al. further disclose that the reactions are performed using a Perkin-Elmer/Cetus DNA thermal cycler. Following the PCR reaction in solution, the contents of the tubes were centrifuged, resuspended and applied to a slide. The PCR-amplified nucleic acid was fixed to the slide and hybridized to $^{125}$I-labelled viral DNA for detection.

Oakes et al. (EP388171) teach purifying single-stranded targeted nucleic acid using non-porous, non-magnetic particles with complementary nucleic acid attached. Oakes et al. claim a method using standard PCR hybridization methodology and include a step of separating the hybrid from the remainder of the specimen with a non-porous, non-magnetic particle. Oakes et al. indicate that the invention is useful since purified nucleic acids can be rapidly and simply purified. Once purified, the hybrids can be amplified by polymerase chain reaction.

Wang et al. (WO9102817) claim a method for quantifying a target nucleic acid segment in a sample. Wang et al. indicates that the invention is useful for determining the quantity of specific RNA molecules in a biological sample.

Gyllensten and Erlich (WO9003444) teach a method for generating single-stranded DNA by PCR that can be linked to an automatic sequence system for rapid sequence determination. The production of single-stranded PCR products using limiting concentrations of one of the two primers is also disclosed.

Innis (WO9003443) teaches a method for structure-independent amplification of DNA by PCR using structure-destabilizing base analog in the amplification reaction. Innis further teaches that the method is useful to increase the specificity of PCR on nucleic acid templates that contain secondary structure and/or compressed regions.

Manos et al. (WO9002821) teach detecting human papilloma-virus using consensus primers in PCR to amplify particular genomic regions. The patent discloses a PCR reaction using at least a pair of primers complementary to separate strands of HPV DNA which hybridize to it and produce an extension product.

Post et al. (WO9001547) teach isolation of thymidine kinase encoding DNA from herpes virus from degenerate primers and the production of thymidine kinase negative feline herpes virus used to produce a live vaccine.

Erlich et al. (WO8911547) disclose HLA DP genotyping by amplifying target DNA then hybridizing the amplified target to a panel of sequence-specific oligonucleotides. It is disclosed that the method is especially useful for assessing the risk of autoimmune disease.

U.S. Pat. No. 5,008,182 (Kwork et al.) discloses the detection of AIDS-associated virus by PCR in free solution or after immobilization on a solid support.

Until the present invention, there have been no methods which allow in situ PCR amplification of specific DNA fragments in intact cells.

SUMMARY OF THE INVENTION

The present invention is an in situ PCR method that can be utilized to amplify selected genetic regions in intact cells. To that end, the present invention provides methods for identifying cells containing at least one selected nucleic acid sequence comprising: (a) fixing cells to a solid support; (b) carrying out a polymerase chain reaction by contacting cells and a selected nucleic acid sequence or sequences with oligonucleotide primers complementary to regions of the selected nucleic acid sequence to form a hybrid and generating an extension product; (c) separating the extension product generated in step (b) to provide single-stranded nucleic acid molecules of the selected nucleic acid sequence; (d) repeating steps (b) and (c) to amplify said selected nucleic acid sequence; (e) hybridizing labelled probe to at least one amplified nucleic acid sequence; and (f) observing labelled cells. The present invention may have application in the diagnosis of HIV-1 infection in individuals and for the determination of the prognosis of AIDS patients. In a preferred embodiment the present invention can be used to determine the proportion of PBMC carrying HIV-1 provirus and proviral sequences isolated from infected individuals. In addition, this invention has broad application and can be applied for identification of essentially any gene(s); bacterial, viral, fungal, parasitic, aberrant genes, oncogenes, normal human genes, genetic defects, genetic markers (i.e., ALA haplotypes, other transplantation genes, blood groups and subtypes, rare genetic events (like translocation of genes), cancer markers, presence of certain genetic predilections (i.e., Alzheimer disease, cystic fibrosis, etc.) and many others.

DETAILED DESCRIPTION OF THE INVENTION

Figure 1:
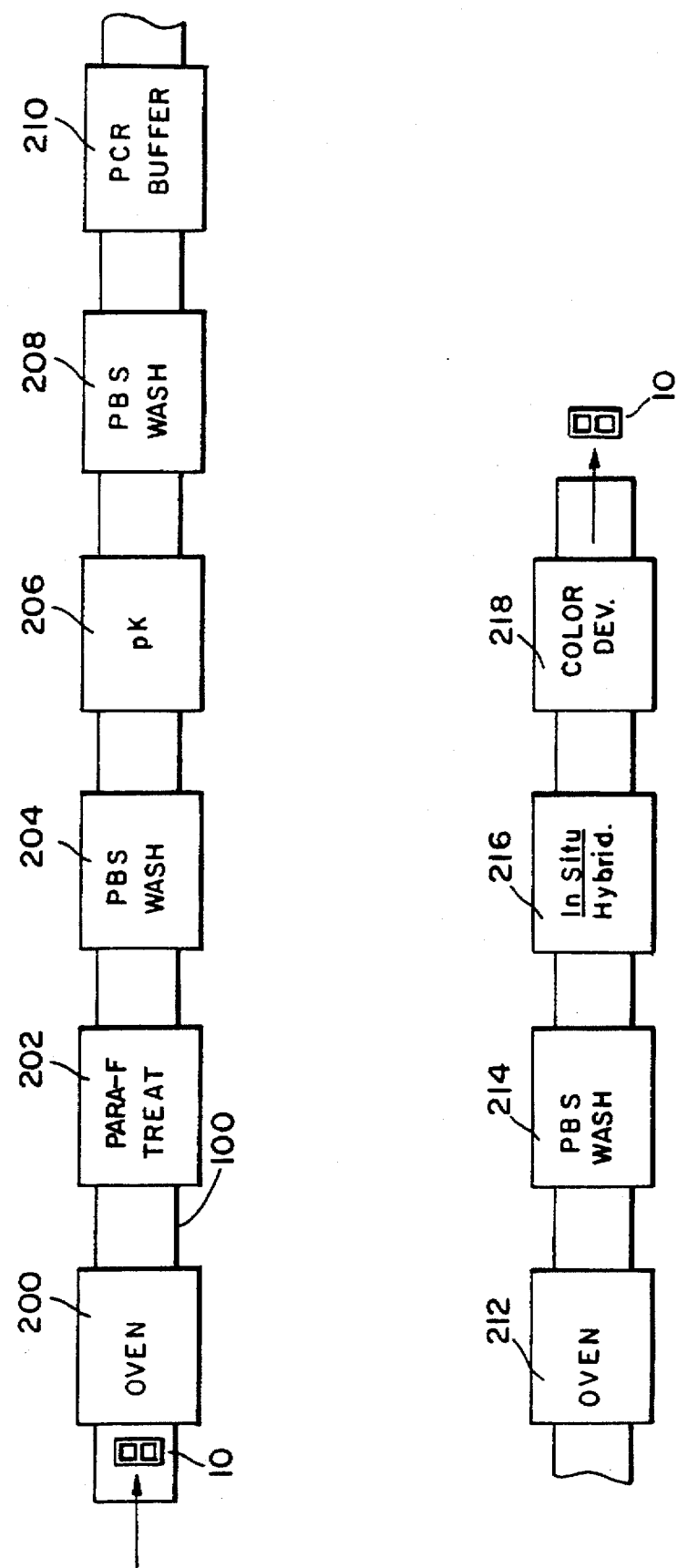
FIG. 1 is a schematic representation of a preferred embodiment of an apparatus for carrying out the methods of the present invention.

In the present invention intact fixed cells function as amplification vessels. Once cells are heat-fixed and permeabilized by paraformaldehyde, PCR reagents, including Taq DNA polymerase and PCR primers, are allowed to diffuse into the cell. Following amplification steps, most of the amplified PCR product remains within the nucleus of the cell due to certain favorable conditions provided by the present invention. It is believed that the amplified PCR product remains bound to either the nuclear double membranes and nuclear matrix, or exists within the cytoplasmic membrane.

The present invention provides methods for identifying cells containing at least one selected nucleic acid sequence comprising: (a) fixing cells to a solid support by exposing the cells to dry heat, for example; (b) carrying out a polymerase chain reaction by contacting cells and selected nucleic acid sequence or sequences with oligonucleotide primers complementary to regions of the selected nucleic acid sequence or sequences to form a hybrid and generating an extension product; (c) separating the extension product generated in step (b) from the template to provide single-stranded nucleic acid molecules of the selected nucleic acid sequence or sequences; (d) repeating steps (b) and (c) to amplify said selected nucleic acid sequence; (e) hybridizing labelled probe to at least one amplified nucleic acid sequence; and (f) observing labelled cells. At least one of the selected nucleic acid sequence or sequences derive from a human virus. In the invention, at least one of the selected nucleic acid sequence or sequences derived from a human virus may be derived from recombinants, mutants or variants of such human virus. The present invention also provides methods whereby at least one of the selected nucleic acid sequences derived from a human virus are derived from a human retrovirus. In a preferred embodiment of the present invention, at least one of the selected sequences derive from human immunodeficiency virus, and comprise one of the following sequences: long terminal repeat (LTR) sequence; the tat gene sequence; the gag gene sequence; the pol gene sequence or the env gene sequence. Methods of the present invention further contemplate that at least one of the sequences utilized in the polymerase chain reaction derived from human immunodeficiency virus are proviral nucleic acid sequences. Methods using oligonucleotide primers derived from sequences complementary to sequences of HIV-1 or HIV-2 virus are also contemplated. Furthermore, the present invention provides methods whereby at least one of the sequences complementary to the sequences of HIV-1 or HIV-2 is derived from recombinants, mutants or variants of HIV-1 or HIV-2.

The present invention uses probes that serve as internal controls in the polymerase chain reaction. Control probes may be complementary to either chromosomal or episomal targeted nucleic acids and serve as positive controls for the polymerase chain reaction; control probes may not be complementary to either chromosomal or episomal targeted nucleic acids and serve as a negative controls for the polymerase chain reaction. In a preferred embodiment, oligonucleotide primers utilized in the polymerase chain reaction comprise nucleic acid sequences complementary to HLA-DQα or SK-19; HLA-DQα or SK-19 probes may be as internal controls in a mixed probe reaction comprising probes complementary to other target sequences.

Methods of the present invention provide that cells utilized in the in situ polymerase chain reaction may be obtained from mammalian tissues, particularly but not limited to human tissues. More specifically, these tissues may be obtained as diagnostic specimens. Further, the cells may be obtained from tissue aspirates and bodily fluids. Cells that are transformed, hyperplastic or obtained from carcinomas are also contemplated to be useful in the methods of the present invention. In a preferred embodiment, cells used in the polymerase chain reaction are human blood cells, particularly but not limited to human peripheral blood monocytic cells; human peripheral blood monocytic cells utilized in methods of the present invention are human blood cells infected with human immunodeficiency virus, including HIV-1 and HIV-2.

In the present invention, solid supports capable of binding cells are employed; teflon is preferred. In a more preferred embodiment, a solid support comprises teflon and glass. Solid supports may be in the form of microscope slides comprising teflon and glass.

To demonstrate the invention, in situ PCR was performed by mixing latently HIV-1-infected U1 monocytoid cells, Folks et al., *Science*, 238:800–2 (1987), with HIV-1-uninfected U937 monocytoid cells, Sundstrom et al., *Int. J. Cancer*, 17:565–77 (1976), in various proportions. PCR primers specific for, and complementary to, selected sequences, were used. Sequences used for demonstration of the methods of the present invention were derived from HIV-1 and the HLA-DQα gene. It was demonstrated using microscopy, that U1 cells subjected to in situ PCR are all positive for the HIV-1 provirus. Uninfected U937 cells subjected to the same procedure did not demonstrate any HIV-1-positive cells. There was a 1:1 ratio of U1 to U937 cells. In situ PCR results demonstrated infected cell ratios of 1:10 and 1:100 respectively. This concurs with reports which demonstrate that the U1 cells are a latently HIV-1-infected subclone of U937 cells having 2 HIV-1 proviral copies per cell. HLA-DQα primers used as a positive control demonstrated positive amplification in all cells following hybridization with a biotinylated probe complementary to HLA-DQα.

Sensitivity of the in situ PCR methods of the present invention was demonstrated using ACH-2 cells, an HIV-1 latently-infected subclone of the T-lymphocytic cell line, CEM, which contains only one HIV-1 provirus copy per cell. See Clouse et al., *J. Immunol.*, 142:431–8 (1989). ACH-2 cells subjected to in situ PCR were all hybridization-positive and at the same degree of intensity. These cells were mixed in varying proportions with uninfected CEM cells and hybridization was demonstrated by microscopy.

Using the methods of the present invention it has been demonstrated that in situ amplification can be efficiently carried out in cell populations which are known to carry one or two copies of HIV-1 provirus per cell. Modifications of gene amplification methods of the present invention makes in situ PCR several-fold more sensitive than standard DNA-PCR. It has further been demonstrated that amplified DNA of the present invention does not leak out of infected cells and contaminate uninfected cells. This is a surprising result that renders the methods of the present invention useful as sensitive in situ PCR diagnostic assays.

Proportions of PBMC containing HIV-1 provirus were demonstrated over a broad ratio range using in situ PCR methods of the present invention. Table I illustrates the results from the quantitation of HIV-1 provirus in HIV-1 seropositive individuals. Uninfected individuals were used as negative controls. PBMC were isolated from patients, bound to solid supports by fixing, and permeabilized. The in situ PCR analysis was carried out as described for the tissue culture cells, using primers specific for HIV-1. In Table I, a single asterisk indicates that each patient's PBMC obtained from a single phlebotomy were evaluated at least twice using the in situ PCR technique. Double asterisks denote that all five individuals in Stage IV D had Kaposi's Sarcoma and no lymphomas. The letters "ND" indicate that these data have not been determined. Disease stages are indicated by Roman numerals and are described briefly following each designation. The arithmetic mean percentage of HIV-1-positive PBMC is expressed with the standard deviation.

TABLE I

Quantitation of HIV-1 Provirus in HIV-1 Seropositive Individuals

| Modified CDC-HIV Classification | Patient (Coded) | Percentage of HIV-1-Positive PBMC* | Total CD4-Positive T Lymphocyte Counts (per mm$^3$) |
|---|---|---|---|
| HIV-1-seropositive Asymptomatic (Stage II) | MIC | 3.3 ± 1.3 | 339 |
| | STA | 2.7 ± 1.7 | 256 |
| | NOV | 0.15 ± 0.3 | ND |
| | BON | 0.66 ± 0.2 | ND |
| | SAY | 0.5 ± 0.01 | ND |
| | FLE | 0.36 ± 0.2 | ND |
| | SVM | 0.8 ± 0.25 | ND |
| | BOT | 0.9 ± 0.1 | ND |
| | ROY | 0.09 ± 0.02 | ND |
| | BER | 1.6 ± 1.0 | ND |
| | HER | 3.6 ± 2.0 | ND |
| | DUG | 1.1 ± 0.1 | ND |
| | ADA | 0.2 ± 0.06 | ND |
| | MAU | 0.2 ± 0.07 | ND |
| | X | 0.3 ± 0.02 | 349 |
| | Y | 0.3 ± 0.05 | 612 |
| | Z | 0.3 ± 0.06 | 429 |
| | AA | 0.1 ± 0.05 | 1050 |
| | BB | 0.3 ± 0.07 | 572 |
| HIV-1-seropositive Persistent Generalized Lymphadenopathy (Stage III) | EVA | 5.4 ± 1.4 | 28 |
| | SED | 2.8 ± 1.8 | 338 |
| | ROB | 12.0 ± 1.8 | 657 |
| | ANT | 10.7 ± 2.0 | 168 |
| | PAD | 11.8 ± 1.9 | 584 |
| | CHR | 13.5 ± 2.1 | ND |

TABLE I-continued

Quantitation of HIV-1 Provirus in HIV-1 Seropositive Individuals

| Modified CDC-HIV Classification | Patient (Coded) | Percentage of HIV-1-Positive PBMC* | Total CD4-Positive T Lymphocyte Counts (per $mm^3$) |
|---|---|---|---|
| | TTI | 5.3 ± 1.5 | ND |
| | BOR | 6.3 ± 1.5 | ND |
| | ASD | 4.0 ± 2.2 | ND |
| | D | 1.2 ± 0.5 | 21 |
| | N | 7.5 ± 0.6 | 84 |
| | R | 1.3 ± 0.5 | 39 |
| | T | 4.0 ± 1.0 | 336 |
| AIDS (Stages IV A–C) | PAR | 11.2 ± 1.4 | 164 |
| | POP | 8.0 ± 1.6 | 107 |
| | GRE | 7.8 ± 1.3 | 226 |
| | LAN | 11.8 ± 1.9 | 104 |
| | A | 0.13 ± 0.06 | 5 |
| | C | 1.5 ± 0.7 | 30 |
| | E | 1.5 ± 0.7 | 132 |
| | F | 2.1 ± 0.14 | 3 |
| | G | 0.5 ± 0.07 | 6 |
| | H | 0.2 ± 0.05 | 33 |
| | I | 7.3 ± 2.0 | 80 |
| | L | 8.5 ± 0.7 | 144 |
| | M | 5.0 ± 1.0 | 32 |
| | O | 8.0 ± 1.0 | 188 |
| | P | 4.0 ± 0.5 | 180 |
| | Q | 3.0 ± 1.0 | 39 |
| | S | 4.7 ± 0.5 | 448 |
| | V | 1.0 ± 0.2 | 13 |
| | W | 2.0 ± 0.1 | 63 |
| AIDS (Stage IV D)** | DOM | 1.8 ± 0.7 | 22 |
| | DWI | 2.0 ± 0.89 | 290 |
| | BUL | 2.0 ± 0.89 | 20 |
| | B | 0.8 ± 0.1 | 25 |
| | K | 1.2 ± 0.2 | 14 |

The percentage of HIV-1 positive PBMC varied between 0.09% and 13.5%, as shown in Table 1. Nineteen asymptomatic HIV-1-seropositive individuals exhibited a range of 0.09% to 3.6%. Thirteen other HIV-1 infected patients having persistent generalized lymphadenopathy (Stage III), as categorized by the modified CDC HIV-classification system, exhibited 1.3% to 13.5% HIV-1 provirus positive cells. Four of these thirteen individuals (N,R,EVA and ANT) developed oral candida infection (thrush) in addition to persistent generalized lymphadenopathy. Individuals in Stages IV A, B, and C revealed 0.13% to 11.8% of PBMC positive for HIV-1 provirus. By contrast, patients in Stage IV D, demonstrating evidence of Kaposi's Sarcoma (KS), showed relatively low percentages of PBMC positive for HIV-1 provirus ranging from 0.8% to 2.0%. Thus, PBMC from individuals who were in CDC Stage II and were asymptomatic showed relatively low percentages of HIV-1 positive PBMC, as compared to Stages III or IV A–C (p<0.001), as determined by the Student's t test. PBMC from patients classified as CDC Stage IV D (patients with Kaposi's Sarcoma but without opportunistic infection) also exhibited a relatively low percentage of cells infected with HIV-1 (p<0.08). No statistically significant difference in the level of HIV-1 positive PBMC was noted comparing individuals in Stage III versus Stage IV A–C. All eleven HIV-1-seronegative controls were consistently negative by in situ PCR.

Evaluation of the same PBMC from HIV-1-seropositive individuals utilizing standard in situ hybridization techniques revealed only 1 in $5 \times 10^3$ to $1 \times 10^5$ PBMC positive for HIV-1-specific nucleic acids. These results were consistently observed utilizing gag, tat and LTR probes and primers. Thus, the vast majority of HIV-1-infected PBMC in vivo do not express large quantities of HIV-1-RNA or are actively producing high levels of virus.

The ability to detect a significantly higher level of HIV-1-infected cells using in situ PCR of the present invention as compared to using other techniques, such as viral culture or standard DNA-PCR, is based on the exquisite sensitivity of this technique. It is believed that a reason for the unusually high sensitivity of the in situ PCR methods of the present invention as compared to the standard DNA-PCR method is that there is no dilution of HIV-1 into non-HIV-1 containing DNA. Such dilution lowers PCR sensitivity. In the in situ PCR methods provided, a cell is believed to be an ultra-small amplification container, where amplification of a DNA segment can be carried out in a concentrated fashion and without dilution with other DNA.

The large numbers of provirus-positive PBMC in the blood of HIV-1-infected individuals suggests that some of these proviruses may be transcriptionally quiescent or latent in vivo. This demonstration of proviral latency in vivo is pertinent to the understanding of HIV-1 pathogenesis. A molecular mechanism of HIV-1 proviral latency has been described although latent infection prior to proviral integration may also exist.

The demonstration of significantly higher numbers of PBMC harboring HIV-1 provirus obtained using the methods of the present invention, as compared to levels of infectious HIV-1 per PBMC in co-culture assays, indicates that some HIV-1 proviral copies may either be defective or maintained in cells not activated to produce virions in cell cultures. Defective HIV-1 proviral copies have been demonstrated in vivo. Therefore, the evaluation of proviral latency and defective viral genomes in vivo remain important areas in the study of the complex pathogenesis and natural history of clinical HIV-1 infection. The ability to precisely measure HIV-1 proviral load in the peripheral blood in vivo is critical to evaluation of the clinical efficacy of therapeutic interventions and as a prognostic indicative of HIV-1 disease progression.

In situ PCR methods of the present invention have allowed quantitation of the percent of cells positive for HIV-1 provirus and have shown a relationship to the stage of HIV-1 clinical infection. This observation has important implications in the determining the prognosis of a patient's disease. Patients in CDC Stage II had a significantly lower percentage of HIV-1-positive PBMC than those in Stage III and Stages IV A–C. Patients in Stage IV D (KS only) had relatively low numbers of HIV-1-infected cells. This finding is rather surprising, and it may be one of the reasons that some investigations have failed to observe the correlation between the clinical stage of HIV-1 infection and the degree of DNA-PCR amplification. This may also account for the longer life span of patients with KS, as compared to other patients with AIDS.

One of the main concerns of investigators utilizing the standard DNA-PCR method is false positive results due to contamination of samples by HIV-1-positive amplified genetic segments. However, the use of in situ PCR methods of the present invention greatly diminishes such concerns since it is believed that contamination of amplified genetic segments will contaminate only a few cells. It is believed that these few contaminated cells will not provide totally false positive results as is the case for standard DNA-PCR methods where combined amplification products are measured in toto.

In situ PCR methods provided by the present invention, which allow amplification of specific DNA fragments in intact cells, have great potential for determining the actual peripheral blood proviral load in various stages of HIV-1 infection and in evaluating the efficacy of various therapeutic interventions. In addition, there is currently no reliable way to determine the states of HIV-1 infection in infants born to HIV-1-seropositive mothers, soon after birth. Methods in the present invention may be useful to identify such infected infants. It is also believed that the methods of the present invention could be utilized to identify contaminated donated blood form individuals who have not yet seroconverted.

Another aspect of the present invention is that the methods disclosed herein lend themselves to automation and, accordingly, the present invention provides apparatus for performing in situ PCR. Referring to FIG. 1, there is shown a schematic representation of an apparatus made in accordance with the present invention. In a most preferred embodiment, specially designed slides 10 that have two wells formed therein are used as cell containers. Cells or tissue sections to be tested in a specific gene or genes are placed in the wells in the slides 10. These cells or tissue specimens are then sequentially processed in one or more separate chambers or other apparatus. Preferably, as shown in FIG. 1, the slide 10 is placed upon a transfer means such as a conveyor belt 100 that moves the slide 10 to the various section of the apparatus that are discussed in detail below. It should be understood, however, that the sequence of operations set forth herein is exemplary and neither the combination of apparatus nor the steps illustrated and described are meant to limit the scope of this aspect of the present invention. Moreover, although the description below is directed toward describing the processing of a single slide, it will be understood that a plurality of slides can be processed together and that certain operations may be performed in parallel upon different batches of slides.

In a preferred embodiment of the apparatus of the present invention a slide 10 (or a plurality of slides 10) enters an oven 200 for heat fixating, preferably at about 105° C. for about 90 seconds. The slide is then placed in a paraformaldehyde treatment apparatus 202 at a temperature of about 37° C. for about two hours. Those of ordinary skill will realize that the time and temperature requirements of the process dictate that this section of the apparatus will be thermally controlled.

After the paraformaldehyde treatment is completed, the slide 10 is transferred to a washing station 204 that most preferably washes the slide three times with a phosphate buffered saline (PBS) washing solution for about 10 minutes. Two consecutive single 10 minute PBS washes follow the first triple wash. Although the washing station 202 is illustrated as a single element of the apparatus, it will be understood that numerous configurations comprising several washing stations could be used to facilitate throughput. After the washings are completed, the slide 10 is moved to a proteinase K (pk) treatment apparatus 206 and treated at 55° C. for up to three hours, depending on the type of specimen contained in the slide 10. As mentioned above, the elevated temperature at which the proteinase K treatment is carried out requires that the apparatus comprise a thermally controlled (heated) zone.

The slide 10 is then transferred to a washing station 208 and is most preferably single washed using a PBS solution. The washing also results in the heat inactivation of the proteinase K. Although the washing station 208 is depicted as a separate portion of the apparatus of the present invention, it should be understood that the washing station 202 or another single wash station could be implemented by routing the transfer means 100 differently. In other words, the embodiment illustrated in FIG. 1 is constructed as a linear array and thus, a separate washing station 208 is shown. The slide is then take from the washing station 208 and transferred to buffer apparatus 210 where PCR buffers, primers, nucleotides and heat stable polymers are added to the slide walls to form a "cocktail." For the purpose of the present invention, "buffering apparatus" therefore is adopted to add one or more of these to the cells.

The slide 10 containing this cocktail is then thermally cycled by transferring it into an oven 212. As was the case with the washing stations 204, 210, the oven 212 need not be a separate piece of apparatus. As illustrated, the slide 10 could instead be transferred back to the oven 200 in which the heat fixation described above was performed. In any event, thermocycling is preferably undertaken for about thirty cycles between temperatures of 95° C., 42° C., and 72° C., for 1 minute each. However, temperature and cycle time may vary according to primers and DNA to be amplified.

After thermal cycling, the slide 10 is again transferred to a wash station 214 which is again most preferably a separate single wash PBS station 214. After the wash is completed, the slide 10 is transferred to a chamber containing the appropriate apparatus to effect in situ hybridization with specific and non-specific probes. Thus, after this step is complete, the slide 10 is transferred to a means for developing the color in the slides 218 using techniques well known to those of skill in the art. The developed slides are then dried and mounted to permit them to be read using either light microscopy or image analysis.

The embodiment of the apparatus illustrated in FIG. 1 is based upon the concept of a linear "production line" that would be able to process a plurality of slides in an automated fashion. However, as well known to those familiar with laboratory automation, the implementation of such a fixed production line requires a significant investment of both time and money. Moreover, the resulting apparatus is relatively difficult to adapt, should the processing steps be modified. Thus, in certain instances, it may be desirable to implement the apparatus of the present invention by using a flexible automation element such as a programmable robotic manipulator that has the various "stations" or chambers described above arrayed around the manipulator, within its reach envelope. Such a flexible system would admit to numerous variations and may permit the elimination of certain of the duplicate elements shown in FIG. 1. Those of skill in the art of designing such equipment could program a robot and design interfaces to permit the methods of the present invention to be carried out in an effective manner.

Having generally described the invention, a more complete understanding can be obtained by reference to the following examples which are provided for purposes of illustration only and are not intended to be limiting.

EXAMPLES

Example 1

Obtaining and Processing Blood Specimens

Blood specimens were obtained from 56 HIV-1-seropositive adults. Nineteen patients were asymptomatic, while thirty-seven were symptomatic. Heparinized peripheral blood specimens were obtained form each individual and assigned a code, then forwarded for laboratory analysis. Blood specimens were also drawn from eleven HIV-1-seronegative individuals. Identity and HIV-1 serological status remained unknown to the MRL, until the completion of the studies.

Blood samples were processed within 4 hours after venipuncture and PBMC were isolated by Ficoll-Hypaque gradient centrifugation. Cells were washed twice with phosphate-buffered saline (PBS) and placed on slides for in situ PCR, as described below.

Example 2

In Situ Polymerase Chain Reaction

To perform in situ PCR for detection of HIV-1 provirus, cells ($1 \times 10^5$ cells per ml) were seeded into the wells of specially designed heavy teflon coated (HTC) slides (Cell-line Associates, Inc. Newfield, N.J. 08344 CAT #10–12, 14 mm wells). Slides were air dried and the placed sequentially, first on a heat block at 105° C. for 90 seconds and then in 1% paraformaldehyde-phosphate-buffered saline (PBS) solution (pH 7.4) for 1 hour. Paraformaldehyde was inactivated by washing the slides in 3 X PBS, then the slides were washed 3 times in 1 X PBS. Endogenous peroxidase activity was removed by quenching the specimens with a 3% solution of hydrogen peroxidase, overnight, at 37° C. The slides were then treated with Proteinase K (60 µg/ml in PBS) for 2 hours at 55° C. Proteinase K was inactivated by placing the slides on a heat block at 90° C. for 2 minutes and, finally, the slides were washed in distilled water and air dried.

The cells were then subjected to amplification. A primer pair, complementary to conserved regions of HIV-1 gag (SK38; nucleotides: 1551–1578; SK39; nucleotides: 1638–1665, Synthetic Genetics, San Diego, Calif.), was used for amplification of HIV-1-DNA. Fifteen µl of a PCR-reaction mixture containing 10 µM of dATP, dCTP, dGTP and dTTP, 20 µM of each primer, 50 mM KCL, 10 mM Tris (pH 8.3), 2.5 MM $MgCl_2$ and 1.0 µl Taq polymerase (1 U/µl, Gene Amp, Cetus), was added to the top two wells of each slide, whereas the bottom well received a PCR-mixture lacking the primers. These slides were covered with 22×60 mm coverslips. Coverslips were sealed with a clear nail polish. Slides were placed on an automatic thermocycler (M.J. Research Boston, Mass.) and amplification was carried out at 94° C./45° C./72° C. for 1 minute each, for 30 cycles. The primers for HLA-DQα (HLA-DQ-GH-26/27, Synthetic Genetics), with a biotinylated probe for HLA-DQα, were used as positive controls.

Example 3

Probing In Situ PCR Extension Products

After amplification, all slides were washed in 2 X SSC buffer (0.3M NaCl and 0.03M Na-citrate) and amplification products were detected by a biotinylated oligonucleotide (SK 19, nucleotides: 1595–1635: Synthetic Genetics), utilizing the in situ hybridization method. Hybridization mixture contained 15–25 pg of biotin-labelled probe, 10 mM DTT, 2 X SSC, fragmented salmon sperm DNA (1 mg/ml), 50% formaldehyde, 2% bovine serum albumin, and E. coli transfer-RNA (1 mg/ml). The mixture was applied to each well of the slide. Slides were sealed with coverslips and incubated on a heat block at 92° C. for 5 minutes. Slides were then transferred to another heated humidified chamber at 48° C. for 4 hours. These slides were thoroughly washed with PBS and then incubated with streptavidin peroxidase complex (100 µg/ml in PBS, pH 7.2) for 1 hr at 37° C. After incubation, slides were thoroughly washed with phosphate buffered saline (PBS). The color was developed with 3' amino 9' ethylene carbozone (AEC) in the presence of 0.03% hydrogen peroxide in 50 mM acetate buffer (pH 5.0) for 10 minutes at 37° C. The slides were then washed and coverslips were applied, with a 50% solution of glycerol/PBS. Slides were analyzed using optical microscopy.

In all amplifications, one slide well was used as an internal control, in which amplified cells were hybridized with a unrelated probe. Hybridization with an unrelated probe (HLA-DQα) gave negative results, whereas with a related probe (SK-19), the technique yielded the expected results. An HIV-1-specific probe (tat gene probe) complementary to a region of HIV-1 not amplified by the gag primers yielded very few positive cells. Other HIV-1-specific sets of primers and probes (long terminal repeat (LTR) and tat) gave consistent results in the assay system of the present invention. U1 and ACH-2 cells evaluated using cytomegalovirus-specific primers and probes yielded no detectable positively staining cells.

Example 4

Statistical Analyses

The arithmetic mean percentage of HIV-1-positive PBMC determined using the methods of the present invention is expressed with the standard deviation. The Student's t-test was used to compare differences in HIV-1-infected PBMC among different groups of individuals whose PBMC were analyzed.

What is claimed is:

1. A method for identifying a cell containing at least one copy of a selected nucleic acid sequence comprising:
    (a) exposing said cell to dry heat thereby fixing said cell to a solid support to produce a heat fixed immobilized cell;
    (b) contacting said heat fixed immobilized cell with paraformaldehyde to produce a paraformaldehyde treated, heat fixed immobilized cell;
    (c) contacting said paraformaldehyde treated, heat fixed immobilized cell containing selected nucleic acid sequence or nucleic acid sequences with oligonucleotide primers complementary to regions of selected nucleic acid sequence or sequences to form a nucleic acid hybrid and generating an extension product by amplification in said cell;
    (d) separating into single stranded nucleic acid molecules, the extension product generated in step (c) to provide single-stranded nucleic acid molecules of the selected nucleic acid sequence or sequences in said cell;
    (e) repeating steps (c) and (d) to amplify said selected nucleic acid sequence or sequences;
    (f) hybridizing a labeled nucleic acid probe to said amplified selected nucleic acid sequence or sequences provided in step (e); and
    (g) observing a labeled cell produced in step (f), wherein a labeled cell indicates a cell containing at least one copy of a selected nucleic acid sequence.

2. The method of claim 1 wherein at least one of the selected nucleic acid sequences derive from a human virus.

3. The method of claim 2 wherein at least one of the selected nucleic acid sequences derive from human immunodeficiency virus and comprise one of the following sequences: long terminal repeat (LTR) sequence; the tat gene sequence; or the gag gene sequence.

4. The method of claim 2 whereby at least one of the selected nucleic acid sequences are proviral nucleic acid sequences.

5. The method of claim 1 wherein said oligonucleotide primers are derived from sequences complementary to sequences of HIV-1 or HIV-2.

6. The method of claim 2 wherein at least one of said nucleic acid sequences is derived from recombinants, mutants or variants of said human virus.

7. The method of claim 1 wherein said oligonucleotide primers are derived from sequences complementary to HLA-DQα or SK-19.

8. The method of claim 1 wherein said cells are human cells.

9. The method of claim 8 wherein said cells are human peripheral blood lymphocytic cells.

10. A method for identifying a cell containing at least one copy of a selected nucleic acid sequence comprising:

(a) exposing said cell to dry heat thereby fixing said cell to a solid support;

(b) paraformaldehyde treating said heat fixed cell;

(c) contacting said heat fixed, paraformaldehyde treated cell containing selected nucleic acid sequence or nucleic acid sequences with a single primer pair complementary to regions of selected nucleic acid sequence or sequences to form a nucleic acid hybrid and generating an extension product by amplification in said cell;

(d) separating into single stranded nucleic acid molecules, the extension product generated in step (c) to provide single-stranded nucleic acid molecules of the selected nucleic acid sequence or sequences in said cell;

(e) repeating steps (c) and (d) to amplify said selected nucleic acid sequence or sequences;

(f) hybridizing a labeled nucleic acid probe to said amplified selected nucleic acid sequence or sequences provided in step (e) in said cell; and (g) observing a labeled cell produced in step (f), wherein said labeled cell indicates a cell containing at least one copy of a selected nucleic acid sequence.

11. The method of claim 10 wherein said oligonucleotide primers are fully complementary to regions of selected nucleic acid sequence or sequences that consist of at least 10 nucleotides.

12. The method of claim 11 wherein said oligonucleotide primers are fully complementary to regions of selected nucleic acid sequence or sequences that comprise 10–30 nucleotides.

13. The method of claim 1 wherein said oligonucleotide primers are fully complementary to regions of selected nucleic acid sequence or sequences that consist of at least 10 nucleotides.

14. The method of claim 13 wherein said oligonucleotide primers are fully complementary to regions of selected nucleic acid sequence or sequences that comprise 10–30 nucleotides.

15. The method of claim 10 wherein said amplification comprises the polymerase chain reaction.

16. The method of claim 1 wherein said amplification comprises the polymerase chain reaction.

* * * * *

UNITED STATES PATENT AND TRADEMARK OFFICE
CERTIFICATE OF CORRECTION

PATENT NO. : 5,750,347
DATED : May 12, 1998
INVENTOR(S) : Bagasra, et al.

It is certified that error appears in the above-indentified patent and that said Letters Patent is hereby corrected as shown below:

At Column 1, line 6, delete "application 07/829,921" and insert therefor -- application 07/829,912 --.

At Column 1, line 50, delete "viva" and insert therefor -- vivo--.

Signed and Sealed this

Twenty-ninth Day of September, 1998

Attest:

BRUCE LEHMAN

Attesting Officer            Commissioner of Patents and Trademarks